United States Patent [19]

Drake et al.

[11] Patent Number: 4,620,016

[45] Date of Patent: Oct. 28, 1986

[54] PREPARATION OF BUTYROLACTONE BY CATALYTIC HYDROGENATION OF SUCCINIC ANHYDRIDE

[75] Inventors: Charles A. Drake; Marvin M. Johnson, both of Bartlesville, Okla.

[73] Assignee: Phillips Petroleum Company, Bartlesville, Okla.

[21] Appl. No.: 734,506

[22] Filed: May 16, 1985

[51] Int. Cl.⁴ ............................................ C07D 307/32
[52] U.S. Cl. .................................................... 549/325
[58] Field of Search ........................................ 549/325

[56] References Cited

U.S. PATENT DOCUMENTS

| | | | |
|---|---|---|---|
| 3,312,718 | 4/1967 | Woskow | 260/343.6 |
| 3,492,314 | 1/1970 | Asano et al. | 260/343.6 |
| 3,829,448 | 8/1974 | Kanetaka et al. | 260/343.6 |
| 4,048,196 | 9/1977 | Broecker et al. | 260/346.11 |
| 4,083,809 | 4/1978 | De Thomas et al. | 252/457 |
| 4,096,156 | 6/1978 | Freudenberger et al. | 260/343.6 |
| 4,155,919 | 5/1979 | Ramioulle et al. | 260/346.11 |
| 4,361,705 | 11/1982 | Marcelin et al. | 564/462 |

*Primary Examiner*—Norma S. Milestone
*Attorney, Agent, or Firm*—K. K. Brandes

[57] ABSTRACT

A process for preparing primarily gamma-butyrolactone comprises the step of contacting under suitable reaction conditions a succinic anhydride containing feed stream with hydrogen gas, in the presence of a catalyst comprising metallic nickel and an aluminum phosphate containing support.

13 Claims, No Drawings

PREPARATION OF BUTYROLACTONE BY CATALYTIC HYDROGENATION OF SUCCINIC ANHYDRIDE

BACKGROUND OF THE INVENTION

This invention relates to a process for preparing gamma-butyrolactone by hydrogenation of succinic anhydride. In another aspect, this invention relates to a catalytic process for making gamma-butyrolactone.

Processes for the catalytic hydrogenation of succinic anhydride to gamma-butyrolactone are known. U.S. Pat. Nos. 3,312,718 and 3,829,448 disclose hydrogenation processes employing nickel-based catalysts. However, there is an ever present need to develop new processes utilizing catalysts that are highly selective for the production of gamma-butyrolactone, thus minimizing the formation of undesirable by-products.

SUMMARY OF THE INVENTION

It is an object of this invention to provide a catalytic process for selectively hydrogenating succinic anhydride to gamma-butyrolactone. It is another object of this invention to provide a process employing new nickel-based hydrogenation catalysts that are more selective to making gamma-butyrolactone than previously known nickel-based catalysts. Other objects and advantages will be apparent from the detailed description and the appended claims.

In accordance with the present invention, a feed stream comprising succinic anhydride is contacted with a free hydrogen containing gas in the presence of a catalyst composition comprising (a) nickel metal, and (b) an aluminum phosphate-containing support, under such reaction conditions as will result in a reaction product comprising gamma-butyrolactone as the major component. Preferably over 50 weight-% of the reaction product is gamma-butyrolactone. In one preferred embodiment, a reactant stream comprising succinic anhydride is hydrogenated over one of the above-cited catalyst compositions at an elevated temperature and an elevated pressure. In another embodiment, the catalyst composition further comprises (c) at least one metal or oxide of a metal selected from the group consisting of alkali metals (preferably Na), alkaline earth metals (preferably Mg), copper, silver, lanthanides (preferably Ce), zirconium, chromium and iron. The catalyst composition utilized in this invention are superior to one comprising nickel and silica in that a greater portion of the formed reaction product is gamma-butyrolactone.

DETAILED DESCRIPTION OF THE INVENTION

The catalyst composition employed in the process of this invention, namely the selective hydrogenation of succinic anhydride to primarily gamma-butyrolactone, is a composition comprising (a) substantially metallic nickel, and (b) an aluminum phosphate-containing support. Aluminum phosphate can be prepared by any method, generally by precipitation upon mixing of a solution containing $Al^{+3}$ ions and a second solution containing $H_3PO_4$ or $H_2PO_4^-$ or $HPO_4^{2-}$ or $PO_4^{-3}$ ions at a suitable pH. Examples of such precipitation methods as those described in U.S. Pat. Nos. 4,364,854 and 4,364,855. The preferred support is aluminum phosphate generally having a surface area of at least 30 $m^2/g$ (as determined by the BET/$N_2$ method). A presently preferred aluminum phosphate has an Al:P mol ratio ranging from about 0.8:1 to about 1:1. Before calcining, the formula of the preferred aluminum phosphate is $Al(PO_4)_a(OH)_b$, wherein a is a number ranging from 0.8 to 1 and b=3−3a.

It is within the scope of this ivention to use combinations of aluminum phosphate and other inorganic refractory oxides such as aluminum oxide, alumino-silicate, titanium dioxide, and the like. Optionally, the catalyst composition further comprises (c) at least one metal or an oxide of a metal selected from the Group consisting of alkali metals (preferably Na), alkaline earth metals (preferably Mg), copper, silver, lanthanides (preferably Ce), zirconium, chromium and iron.

The catalyst composition can be prepared by any known method of providing substantially metallic nickel on an alumina phosphate containing support, optionally in conjunction with one or more metals or metal oxides as described in (c). Preferably, the aluminum phosphate containing support material is first impregnated with an aqueous solution containing a suitable nickel compound such as as nickel (II) nitrate, plus optionally a nitrate of the metals listed in (c). The thus impregnated material is calcined at a temperature high enough so as to convert at least a portion of the metal compound, preferably nitrates, to the corresponding oxides. The calcined material is then heated with a reducing gas such as hydrogen so as to substantially reduce the nickel oxide to nickel metal. Copper oxide or silver oxide, if present, will also be substantially reduced to the metal (Cu or Ag). Typical calcination conditions comprise about 300°–400° C. and about 1–5 hours. Typical reducing conditions comprise about 300°–600° C. and about 1–5 hours.

It is within the scope of this invention to employ other methods of depositing nickel and either cerium or zirconium on the silica-containing support. Non-limiting examples of such methods are: impregnation with a solution of one or more solvated metals; impregnation with decomposable metal compounds such as nickel carbonyl and subsequent decomposition by heating; and condensation of nickel metal vapors on the support.

The nickel content (measured as nickel metal) in the catalyst compositions of this invention generally ranges from about 0.2 to about 50 weight-%, preferably from about 1 to about 40 weight-%, and more preferably from about 10 to about 30 weight-%, based on the entire catalyst composition. If a component (c) is also present, the content of the metal or metal oxide ranges from about 0.1 to about 20 weight-%, preferably from about 0.5 to 10 weight-%. The surface area (as determined by the BET/$N_2$ method; ASTM D3037) of the finished catalyst composition generally ranges from about 30 to about 150 $m^2/g$.

The feed stream to be hydrogenated in accordance with the process of this invention can be substantially pure succinic anhydride, or a mixture of succinic anhydride with an inert substance such as a paraffin, or an inert gas, or a mixture of succinic anhydride and gamma-butyrolactone (the desired product), such as a recycle stream from which a portion of butyrolactone has been removed and to which fresh succinic anhydride has been added. The second reactant can be substantially pure hydrogen gas or a mixture of hydrogen and another suitable gas such as an inert gas.

The succinic anhydride containing feed stream, the free hydrogen containing gas stream and the catalyst composition of this invention can be contacted in any suitable manner. Said two streams can be added separately into a suitable reaction vessel and then be contacted in at least partially mixed form with the catalyst composition under suitable reaction conditions. Or the two streams can be premixed and then contacted with the catalyst composition under suitable reaction conditions so as to produce a reaction product comprising gamma-butyrolactone. The process of this invention can be a batch process or a continuous process. In a batch process the process ingredients (succinic anhydride stream, hydrogen stream and catalyst composition) are added in any order to a vessel, preferably equipped with agitating and heating means, and the ingredients are then kept in contact for a certain length of time under suitable conditions so as to produce a product comprising gamma-butyrolactone. In this type of operation, the catalyst can be dispersed in the liquid feed stream (slurry operation) and contacted with hydrogen with agitation (e.g., by means of a mechanical mixer or static mixing means); or the liquid feed stream and hydrogen can be circulated through a fixed bed containing the catalyst composition. In a continuous process, which is presently preferred, the succinic anhydride containing feed stream and the free hydrogen containing gas stream can be passed, at least partially mixed, through a fixed bed containing the solid catalyst composition, under such conditions as will result in a product comprising gamma-butyrolactone. Optionally, an inert solvent can be present during the batch or continuous process.

Heating of the process ingredients is generally required to accomplish at least partial conversion (preferably exceeding 50%) of succinic anhydride to gamma-butyrolactone. Any suitable temperature that will cause and maintain a controllable reaction can be employed. Any feasible heating means can be utilized. It is within the scope of this invention to preheat one or more of the process ingredients before they are introduced into a reactor, which is heated to maintain a suitable temperature. Generally the reaction temperature exceeds about 120° C. and preferably ranges from about 180° C. to about 300° C.

The reaction pressure generally is above atmospheric pressure. The selection of the reaction pressure will greatly depend on the reaction temperature, the feed rates of liquid feed and hydrogen and the specific reactor design. Generally the pressure ranges from about 100 to about 10,000 psig, preferably about 1,000 to about 3,000 psig.

The reaction time, i.e., the time of intimate, simultaneous contact of all process ingredients, can vary from 1 minute to about 50 hours and will preferably be in the range of about 0.2 to about 2 hours. The actual reaction time will greatly depend on the flow rates of the succinic anhydride containing feed stream and of the hydrogen containing gas stream, the selection of an effective, yet safe, reaction temperature, the extent of mixing and agitation (if any) during the reaction, the amount of the catalyst employed, etc.

Any suitable molar ratio of hydrogen to succinic anhydride can be employed. Generally, an excess of hydrogen over what is stoichiometrically required is employed. The exact ratio that should be employed greatly depends on the reaction temperature, pressure and reaction time. Unreacted hydrogen is preferably separated from the reaction effluent and recycled to the hydrogenation reactor.

The formed reaction products, which comprise gamma-butyrolactone, can be separated from the reaction mixture by any suitable separation means such as fractional distillation, or crystallization, or extraction with a suitable solvent (e.g., a liquid paraffin such as n-hexane) plus subsequent evaporation of the solvent. Unreacted process ingredients, particularly succinic anyhydride, are preferably at least partially separated in a similar manner and recycled to the reaction zone with added fresh ingredients. The utility of gamma-butyrolactone is disclosed in U.S. Pat. No. 4,083,809, herein incorporated by reference.

The following examples are presented to further illustrate this invention without unduly limiting the scope of the invention.

EXAMPLE I

This example illustrates the preparation of the nickel catalyst compositions employed in the catalytic hydrogenation of succinic anhydride.

Control Catalyst A was prepared by mixing 100 grams of G57 silica (BET/$N_2$ surface area: 300 $m^2/g$; pore volume: 1.0 cc/g; Na content: 0.1 weight-%; $Al_2O_3$ content: 0.05 weight-%; supplied by Davison Chemical Division of W. R. Grace & Co., Baltimore, MD) with a solution of 100 grams of nickel nitrate in 60 mL $H_2O$. The thus impregnated silica is first partially dried under vacuum conditions in a rotating evaporator, then dried at about 100° C. for 1 hour in air, calcined at about 350° C. for 3 hours, and finally reduced by a flowing hydrogen stream at about 450° C. for 3 hours. Catalyst A had a nickel content of 20.2 weight-% Ni.

Invention Catalyst B was prepared by first dissolving 1230 g of $Al(NO_3)_3\text{-}9H_2O$ and 339.8 g of $NH_4H_2PO_4$ in about 180 mL of water with heating and stirring, and then adding about 700 mL of aqueous ammonium hydroxide solution so as to precipitate an aluminum phosphate gel. The precipitate having an Al/P atomic ratio of about 0.9 was filtered, and the filter cake was divided into two equal parts. Each part was slurried in about 4 liters of distilled water containing 30 mL of a concentrated ammonia solution, and then refiltered. This filter cake was also divided, and each part was slurried in about 4 liters of isopropanol and stirred for about 30 minutes at 75° C. This slurry was filtered, and the filter cake was dried overnight in a vacuum oven and screened through a 35 mesh screen.

98 grams of the dried aluminum phosphate having the approximate formula $Al(PO_4)_{0.9}(OH)_{0.3}$ were impregnated in two stages with a solution of 99.8 grams of $Ni(NO_3)_2\text{-}6H_2O$ in 300 mL of water. The catalyst was first dried overnight in an oven and then calcined at about 490° C. for 3 hours. The calcined material was reduced in a stream of hydrogen at about 420° C. for three hours. The reduced Catalyst B contained about 17 weight-% Ni.

EXAMPLE II

This example illustrates the hydrogenation of succinic anhydride over the nickel catalyst described in Example I. A stainless steel pipe having an inner diameter of about 0.5 inch and a length of about 12 inches was filled with about 40 grams of a catalyst. The reactor was heated by means of electric furnace. A liquid feed stream containing 30 weight-% succinic anhydride and 70 weight-% gamma-butyrolactone was pumped downwardly through the reactor at a feed rate of 1.0 mL/minute. Hydrogen gas was introduced essentially simultaneously with the feed at a rate ranging from about 100 to about 500 Liter/hour. The reactor pressure was about 1500 psig. The liquid product was collected and distilled. The volatile fraction was analyzed by means of a Hewlett-Packard Model 5880 gas chromatograph. Pertinent operating conditions and results are summarized in Table I.

TABLE I

| Run | Catalyst | Temp. (°C.) | H$_2$ Flow (L/Hr.) | % Conversion of Succ. Anhydride | % Selectivity[1] to Butyrolactone |
|---|---|---|---|---|---|
| 1 (Control) | A | 229 | 230 | 99 | 59 |
| 2 (Invention) | B | 218 | 230 | 97 | 74 |
| | B | 223 | 230 | 98 | 80 |
| | B | 227 | 450–500 | 99 | 91 |

[1]Weight % of gamma-butyrolactone in the product divided by % conversion, multiplied by 100.

Data in Table I show that the Ni/AlPO$_4$ catalyst exhibited a greater selectivity to butyrolactone than the Ni/SiO$_2$ catalyst. Conversion of succinic anhydride was comparable in both runs, in spite of the lower surface area of the Ni/AlPO$_4$ catalyst.

EXAMPLE III

This example illustrates the effect of additional catalyst components on the activity and selectivity of supported nickel catalysts during the hydrogenation of succinic anhydride to gamma-butyrolactone, essentially in accordance with the procedure described in Example I. The nickel catalysts were prepared in accordance with the procedure for control Catalyst A (Ni/SiO$_2$), except that the impregnating solutions, which were used in the preparations of those catalysts having a second metal component, contained a salt (generally a nitrate) of said second metal component. After calcination and reduction with hydrogen (as described in Example I), the second metals were present as oxides, except copper and silver of which were at least partially reduced to the metals. Pertinent operating conditions and results are summarized in Table II. All catalysts tested in runs of this example were silica-supported.

TABLE II

| Run | Catalyst | Temp. (°C.) | % Conversion of Succinic Anhydride | % Selectivity to Butyrolactone |
|---|---|---|---|---|
| 1 | 20 wt % Ni | 229 | 99 | 59 |
| 3 | 20 wt % Ni + 1.1 wt % Na | 222 | 99 | 94 |
| 4 | 20 wt % Ni + 2.6 wt % Cu | 238 | 99 | 93 |
| 5 | 20 wt % Ni + 2.6 wt % Ag | 231 | 100 | 79 |
| 6 | 20 wt % Ni + 3.2 wt % Ce | 229 | 100 | 88 |
| 7 | 20 wt % Ni + 3.7 wt % Zr | 210 | 100 | 98 |
| 8 | 20 wt % Ni + 3.2 wt % Cr | 255 | 100 | 80 |
| 9 | 20 wt % Ni + 1.4 wt % Fe | 230 | 100 | 81 |

Data in Table II shows that the presence of a specific second metal in the silica-supported nickel catalysts had a beneficial effect on the selectivity to butyrolactone. Based on these data, it is presently preferred that at least one second metal or an oxide of a second metal selected from the group consisting of Na and other alkali metals, Mg and alkaline earth metals, Cu, Ag, Ce and other lanthanides, Zr, Cr and Fe be present in aluminum phosphate supported nickel catalysts.

Reasonable variations and modifications are possible within the scope of the disclosure and appended claims.

I claim:

1. A process for preparing gamma-butyrolactone comprising the step of contacting a succinic anhydride containing feed stream with a free hydrogen containing gas, in the presence of a catalyst composition selective for the production of gamma-butyrolactone consisting essentially of
   (a) substantially metallic nickel, and
   (b) aluminum phosphate as support, under such conditions as will result in gamma-butyrolactone reaction product.

2. A process in accordance with claim 1, wherein said support is aluminum phosphate having a surface area of at least 30 m$^2$/g.

3. A process in accordance with claim 1, wherein the nickel content ranges from about 0.2 to about 50 weight-%, based on the entire catalyst composition, and the surface area of the catalyst composition ranges from about 30 to about 150 m$^2$/g.

4. A process in accordance with claim 3, wherein the nickel content ranges from about 1 to about 40 weight-%, based on the entire catalyst composition.

5. A process in accordance with claim 3, wherein the nickel content ranges from about 10 to about 30 weight-%, based on the entire catalyst composition.

6. A process in accordance with claim 4, wherein the reaction conditions comprise a temperature ranging from about 180° C. to about 300° C., a pressure ranging from about 100 to about 10,000 psig, and a reaction time ranging from about 1 minute to about 50 hours.

7. A process in accordance with claim 5, wherein the reaction conditions comprise a temperature ranging from about 180° to about 300° C., and a pressure ranging from about 1,000 to about 3,000 psig.

8. A process in accordance with claim 1 wherein said catalyst composition is prepared by first impregnating aluminum phosphate with a solution comprising nickel nitrate, calcining the thus impregnated material at a temperature high enough and a time period long enough to convert at least a portion of nickel nitrate to nickel oxide; and then heating said calcined, impregnated material with hydrogen so as to substantially reduce nickel oxide to nickel metal.

9. A process in accordance with claim 8 wherein said calcining is carried out at a temperature of about 300°–400° C.

10. A process in accordance with claim 8, wherein said heating with hydrogen is carried out at a temperature of about 300°–600° C. and said reducing gas is hydrogen.

11. A process in accordance with claim 1 comprising the additional step of separating gamma-butyrolactone from the reaction mixture.

12. A process in accordance with claim 11, wherein said separating step comprises fractional distillation.

13. A process in accordance with claim 11, wherein said separating step comprises extraction.

* * * * *